(12) United States Patent
Muller-Pathle et al.

(10) Patent No.: US 9,468,719 B2
(45) Date of Patent: Oct. 18, 2016

(54) AUTOINJECTOR

(71) Applicant: SANOFI-AVENTIS DEUTSCHLAND GMBH, Frankfurt am Main (DE)

(72) Inventors: Stephan Muller-Pathle, Frankfurt am Main (DE); Philippe NziKe, Frankfurt am Main (DE); Axel Roth, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 170 days.

(21) Appl. No.: 14/352,358

(22) PCT Filed: Oct. 11, 2012

(86) PCT No.: PCT/EP2012/070110
§ 371 (c)(1),
(2) Date: Apr. 17, 2014

(87) PCT Pub. No.: WO2013/057031
PCT Pub. Date: Apr. 25, 2013

(65) Prior Publication Data
US 2014/0276448 A1    Sep. 18, 2014

(30) Foreign Application Priority Data
Oct. 21, 2011 (EP) .................... 11186229

(51) Int. Cl.
*A61M 5/20*    (2006.01)
*A61M 5/32*    (2006.01)

(52) U.S. Cl.
CPC ......... *A61M 5/2033* (2013.01); *A61M 5/3232* (2013.01); *A61M 5/3234* (2013.01); *A61M 2005/206* (2013.01); *A61M 2005/208* (2013.01); *A61M 2005/2013* (2013.01)

(58) Field of Classification Search
CPC .............. A61M 2005/2013; A61M 2005/206; A61M 2005/208; A61M 5/2033; A61M 5/3232; A61M 5/3234
See application file for complete search history.

(56) References Cited

U.S. PATENT DOCUMENTS

2013/0035664 A1\*   2/2013   Mojdehbakhsh ..... A61M 5/284
                                                             604/506

FOREIGN PATENT DOCUMENTS

| DE | 102007013836 |   | 9/2008 |
| FR | 2506161 |   | 11/1982 |
| WO | 2004/047891 |   | 6/2004 |
| WO | 2007/002052 |   | 1/2007 |
| WO | 2008113199 | \* | 9/2008 |

OTHER PUBLICATIONS

International Search Report for Int. App. No. PCT/EP2012/070110, completed Jan. 7, 2013.

\* cited by examiner

*Primary Examiner* — Rebecca E Eisenberg
(74) *Attorney, Agent, or Firm* — Fish & Richardson P.C.

(57) ABSTRACT

Described is an autoinjector comprising a spring holder, a guide cylinder releasably coupled to the spring holder, a drive assembly releasably coupled to the spring holder, a drive spring adapted to apply a force on the drive assembly, and a penetration spring adapted to apply a force on the guide cylinder. The guide cylinder is adapted to accommodate a syringe having a plunger. The drive assembly is coupled to the guide cylinder and adapted to engage the plunger.

16 Claims, 14 Drawing Sheets

AUTOINJECTOR

CROSS REFERENCE TO RELATED APPLICATIONS

The present application is a U.S. National Phase Application pursuant to 35 U.S.C. §371 of International Application No. PCT/EP2012/070110 filed Oct. 11, 2012, which claims priority to European Patent Application No. 11186229.8 filed Oct. 21, 2011. The entire disclosure contents of these applications are herewith incorporated by reference into the present application.

TECHNICAL FIELD

This application relates to autoinjectors for the administration of a medicament to a patient.

BACKGROUND

Administering an injection is a process which presents a number of risks and challenges for users and healthcare professionals, both mental and physical.

Conventional injection devices typically fall into two categories—manual devices and autoinjectors. In a conventional manual device, a user must provide a force to drive a medicament out of the device, e.g., by depressing a plunger. There are numerous disadvantages inherent with use of a manual device. For example, if the user stops depressing the plunger, less than a full dose of the medicament may be delivered. Further, the force required to depress the plunger may be problematic for elderly users or those with dexterity problems, which may lead to trembling or shaking when aligning or the injection device and/or while administering the dose of the medicament.

Conventional autoinjectors aim to overcome the problems associated with manual devices automating some or all of the functions of the manual devices. There remains a need for an improved autoinjector.

SUMMARY

It is an object of the present invention to provide a novel autoinjector.

In an exemplary embodiment, an autoinjector according to the present invention comprises a spring holder, a guide cylinder releasably coupled to the spring holder, a drive assembly releasably coupled to the spring holder, a drive spring adapted to apply a force on the drive assembly, and a penetration spring adapted to apply a force on the guide cylinder. The guide cylinder is adapted to accommodate a syringe having a plunger. The drive assembly is coupled to the guide cylinder and adapted to engage the plunger.

In an exemplary embodiment, the autoinjector further comprises a rear case adapted to engage the spring holder.

In an exemplary embodiment, the autoinjector further comprises a front case and a needle sleeve telescopically coupled to the front case. In an exemplary embodiment, the autoinjector further comprises a cap detachably coupled to the front case or the needle sleeve.

In an exemplary embodiment, the autoinjector further comprises a trigger button adapted to engage the guide cylinder and the spring holder. The trigger button includes a ramped base adapted to engage ramped latches on resilient arms on the guide cylinder. The ramped latches releasably engage the spring holder. The trigger button includes a stem adapted to engage resilient fingers on the spring holder. The resilient fingers releasbly engage the drive assembly.

In an exemplary embodiment, the drive spring is grounded in a recess in the rear case and the drive assembly. The drive spring is a tension spring.

In an exemplary embodiment, the autoinjector further comprises an auxiliary spring grounded in the drive assembly and adapted to apply a force on the plunger. The drive assembly includes a distal resilient latch adapted to retain the auxiliary spring in a compressed state.

In an exemplary embodiment, the drive assembly includes resilient arms adapted to engage recesses formed in the rear case.

In an exemplary embodiment, the syringe includes a needle retraction mechanism.

In an exemplary embodiment, the rear case includes an enclosed end having a ramped base adapted to engage ramped latches on resilient arms on the guide cylinder and having a stem adapted to engage resilient fingers on the spring holder.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1A:
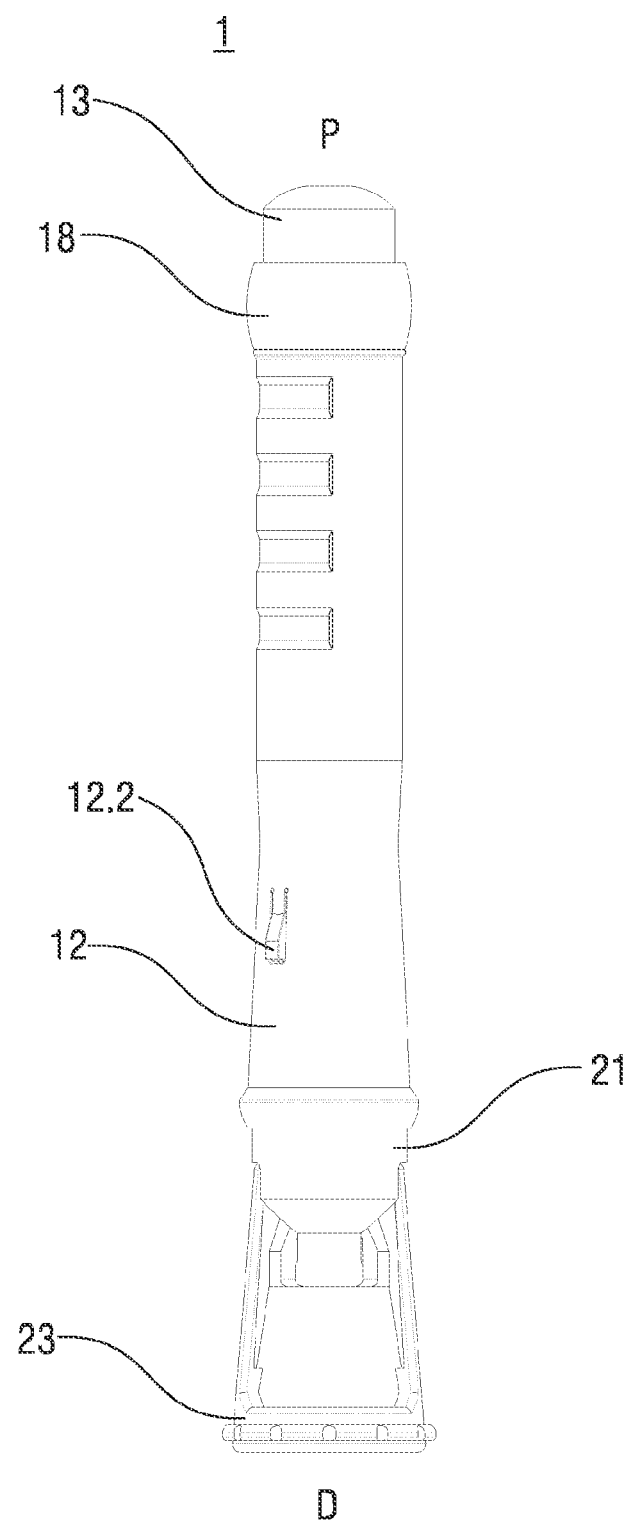
FIG. 1A shows a lateral view of an exemplary embodiment of an autoinjector according to the present invention.
Figure 1B:
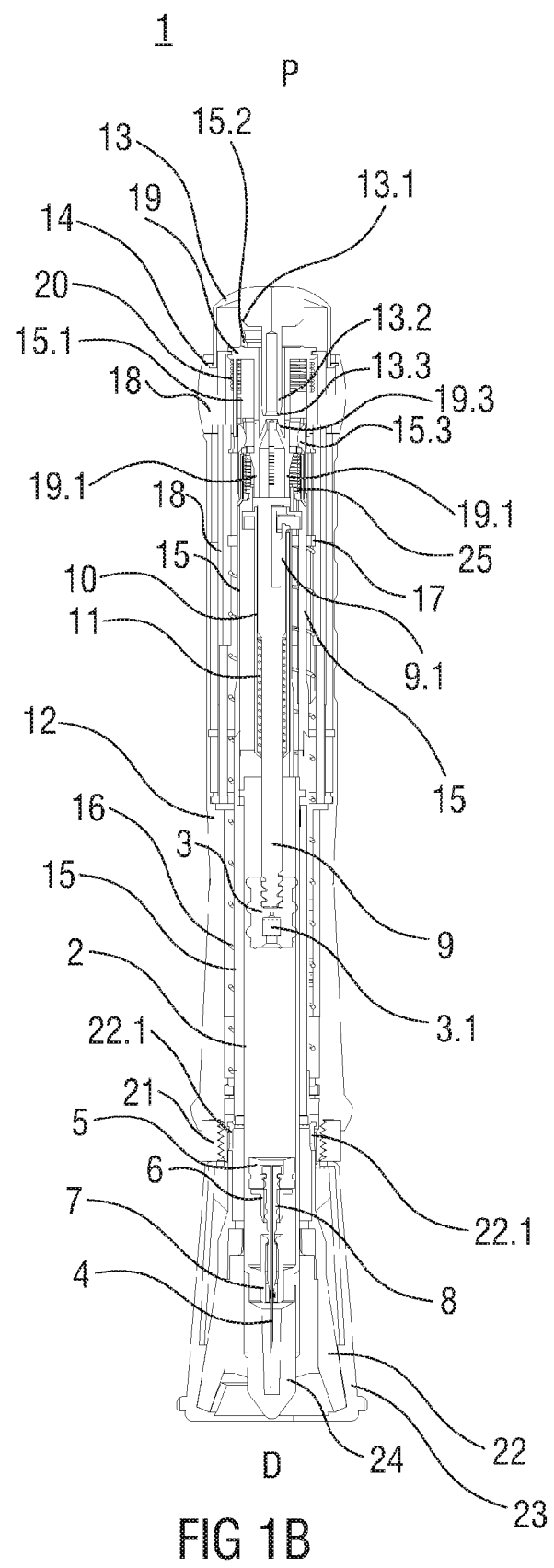
FIG. 1B shows a sectional view of an exemplary embodiment of an autoinjector according to the present invention.

FIG. 1A shows a lateral view of an autoinjector 1 for administering a medicament in an initial state. FIG. 1B shows a respective longitudinal section of the autoinjector 1.

As shown in FIG. 1A, in an exemplary embodiment, the autoinjector 1 comprises a front case 21 that is adapted to engage a rear case 12. When the front case 21 is coupled to the rear case 12, the autoinjector 1 has an elongate casing which can be grasped and held by a user. A cap 23 is detachably coupled to a distal end of the front case 21. In an exemplar embodiment, a lead sleeve 18 is coupled to a proximal end of the rear case 12, and a trigger button 13 is coupled to a proximal end of the lead sleeve 18.

FIG. 1B shows a longitudinal section of an exemplary embodiment of the autoinjector 1. A guide cylinder 15 is adapted to hold a syringe 2, and the guide cylinder 15 can move axially relative to the rear case 12.

In an exemplary embodiment, the syringe 2 may have a needle retraction mechanism. For example, the syringe 2 may be a Unifill or Unitract syringe from Unilife Corporation. The syringe 2 may include a barrel, a stopper 3 slidably arranged within the barrel, and a needle 4 arranged on a distal end of the syringe 2. The syringe 2 may include a needle retraction mechanism comprising a needle seal 5 slidably arranged in a distal end of the barrel, an ejector ring 6 distal of the needle seal 5, a needle retainer 7 arranged on the distal end of the syringe 2 and adapted to engage a needle mount 8 coupled to the needle 4. The stopper 3 includes a cavity 3.1 adapted to engage the needle mount 8, as described in more detail below.

In the exemplary embodiment, the syringe 2 includes an inner plunger 9 telescopically coupled to an outer plunger 10. A distal end of the inner plunger 9 is coupled to the stopper 3. A plunger spring 11 biases the outer plunger 10 relative to the inner plunger 9. A resilient arm 9.1 on the inner plunger 9 engages the inner plunger 9 to the outer plunger 10. A release ring on a finger flange of the syringe 2 is adapted to engage the resilient arm 9.1, causing the arm 9.1 to deflect and disengage the outer plunger 10. When the arm 9.1 disengages the outer plunger 10, the plunger spring 11 expands, and the inner plunger 9 can move axially relative to the outer plunger 10. The outer plunger 10 comprises non return features (not illustrated) for engaging it to the release ring.

When the syringe 2 is assembled, a needle sheath 24 is attached to the needle 4.

In an exemplary embodiment, a drive spring 16 (e.g., a tension spring) is wrapped over the guide cylinder 15. A distal end of the drive spring 16 is grounded in a recess in the rear case 12 while a proximal end of the drive spring 16 is grounded in a drive assembly 17 which is also wrapped over the guide cylinder 15. In use, as described further below, the drive assembly 17 engages the outer plunger 10 of the syringe 2 and moves in a distal direction D relative to the guide cylinder 15. For example, a protrusion on the drive assembly 17 may engage a longitudinal slot in the guide cylinder 15, allowing the drive assembly 17 to move relative to the guide cylinder 15 until the protrusion abuts distal or proximal ends of the slot. The engagement of the protrusion in the slot may also prevent rotation of the drive assembly 17 relative to the guide cylinder 15.

In an exemplary embodiment, two resilient arms 17.1 are distally arranged on the drive assembly 17 for deflecting into recesses 12.1 in the rear case 12 when the drive assembly 17 has distally advanced relative to the rear case 12 (e.g., when the needle 4 has reached a penetration depth). As explained further below, when a used syringe 2 is to be removed from the autoinjector 1, resilient arms 12.2 on the rear case 12 may be pressed to deflect the resilient arms 17.1 out of the recesses 12.1, thereby disengaging the drive assembly 17 from the rear case 12.

In an exemplary embodiment, the lead sleeve 18 is arranged on a proximal end of the rear case 12. The trigger button 13 is arranged in an aperture on a proximal end of the lead sleeve 18. A circlip 14 sits on a distal flange of the trigger button 13. The circlip 14 is has an outer diameter greater than a diameter of the distal flange of the trigger button 13, and abuts against a shoulder adjacent the aperture on the proximal end of the lead sleeve 18 to prevent the trigger button 13 from disengaging the lead sleeve 18.

In an exemplary embodiment, a spring holder 19 is coupled to the lead sleeve 18. The spring holder 19 includes an axial channel for accommodating a stem 13.2 extending in the distal direction D on the trigger button 13. Resilient fingers 19.1 extend axially in the distal direction D from the spring holder 19. Prior to use, the resilient fingers 19.1 engage the drive assembly 17. As explained further below, when the trigger button 13 is pressed, the stem 13.2 moves axially in the axial channel and engages the fingers 19.1, pulling them out of engagement with the drive assembly 17. For this purpose, the distal stem 13.2 and the fingers 19.1 may exhibit ramps 13.3, 19.3 for engaging each other.

The spring holder 19 also includes slots for receiving resilient arms 15.1 extending in the proximal direction P on the guide cylinder 15. Each of the arms 15.1 has a ramped latch 15.2 adapted to engage the spring holder 19. Prior to use, the ramped latch 15.2 engages the slot on the spring holder 19 and extends proximally relative to the spring holder 19. As explained further below, when the trigger button 13 is pressed, a ramped base 13.1 of the stem 13.2 engages the ramped latch 15.2 to deflect the ramped latch 15.2 radially, disengaging the arm 15.1 from the spring holder 19. Prior to use, if the trigger button 13 is pressed, it will abut, without deflecting, the ramped latch 15.2, thus preventing inadvertent firing of the autoinjector 1.

In an exemplary embodiment, a penetration spring 20 is grounded distally on ledges on the proximal arms 15.1 of the guide cylinder 15 and proximally on the spring holder 19. Prior to use, the penetration spring 20 is pre-loaded.

In an exemplary embodiment, an auxiliary spring 25 is arranged on an inner hub of the drive assembly 17. Prior to use, the auxiliary spring 25 is pre-loaded, bearing proximally on a proximal bearing and distally on a distal latch 17.2 (cf. FIG. 6C), which can be disengaged depending on the longitudinal position of the drive assembly 17 in the guide cylinder 15.

In an exemplary embodiment, the front case 21 is coupled to a distal end of the rear case 12, e.g., by threads, bayonet coupling, snap-fit, etc. A needle sleeve 22 is telescoped in, and axially movable relative to, the front case 21. When the autoinjector 1 is assembled, proximally extending arms 22.1 on the needle sleeve 22 may abut a distal end of the guide cylinder 15.

In an exemplary embodiment, the cap 23 engages the needle sheath 24 and is arranged over the needle sleeve 22.

Figure 2A:
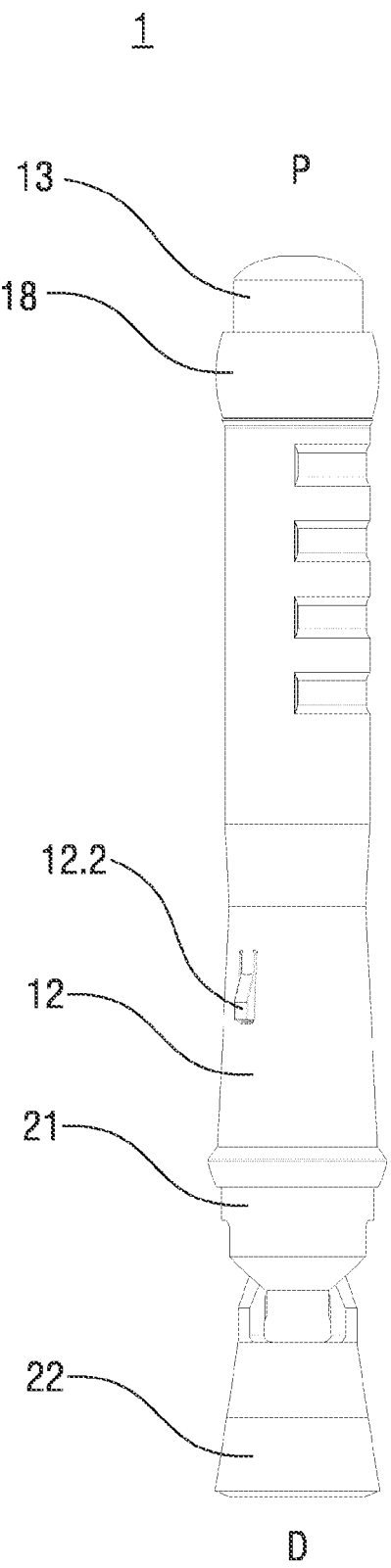
FIG. 2A shows a lateral view of an exemplary embodiment of an autoinjector according to the present invention after removal of a cap.
Figure 2B:
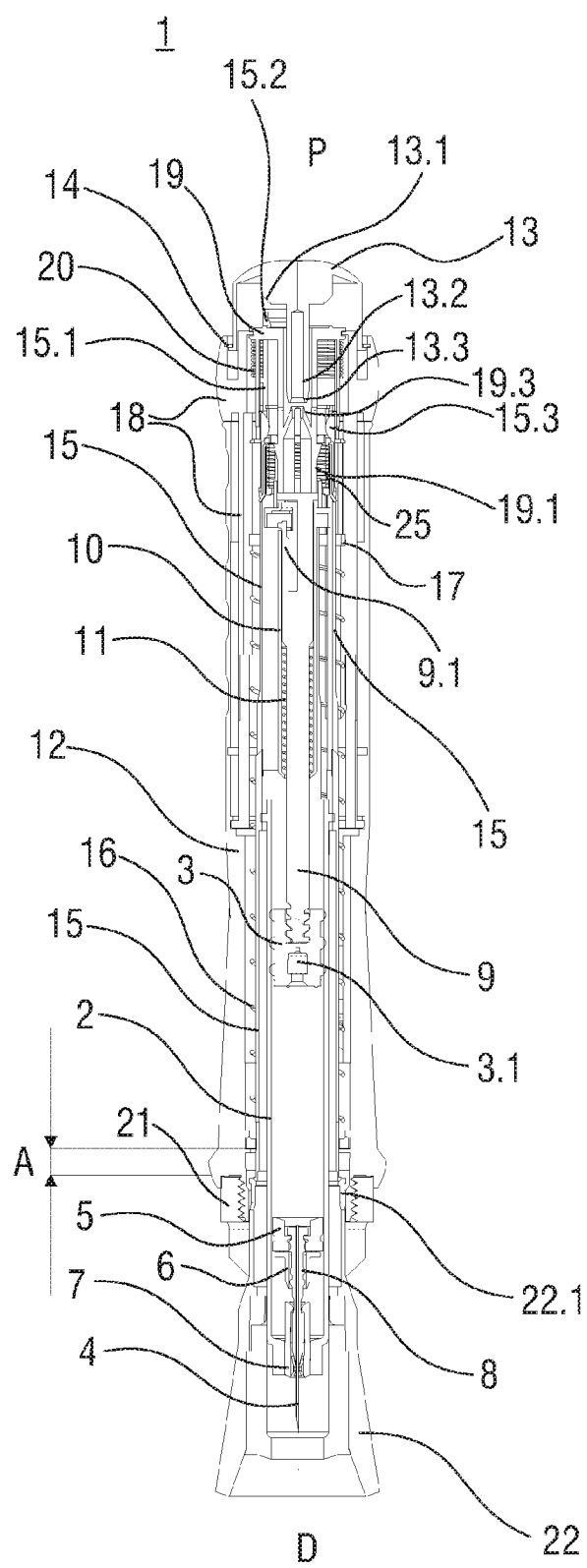
FIG. 2B shows a sectional view of an exemplary embodiment of an autoinjector according to the present invention after removal of a cap.

As shown in the exemplary embodiments in FIGS. 2A and 2B, in order to prepare for an injection, the cap 23 is removed from the autoinjector 1 taking with it the needle sheath 24. Because the arms 15.1 of the guide cylinder 15 have not moved, the trigger button 13 cannot not be depressed.

Figure 3A:
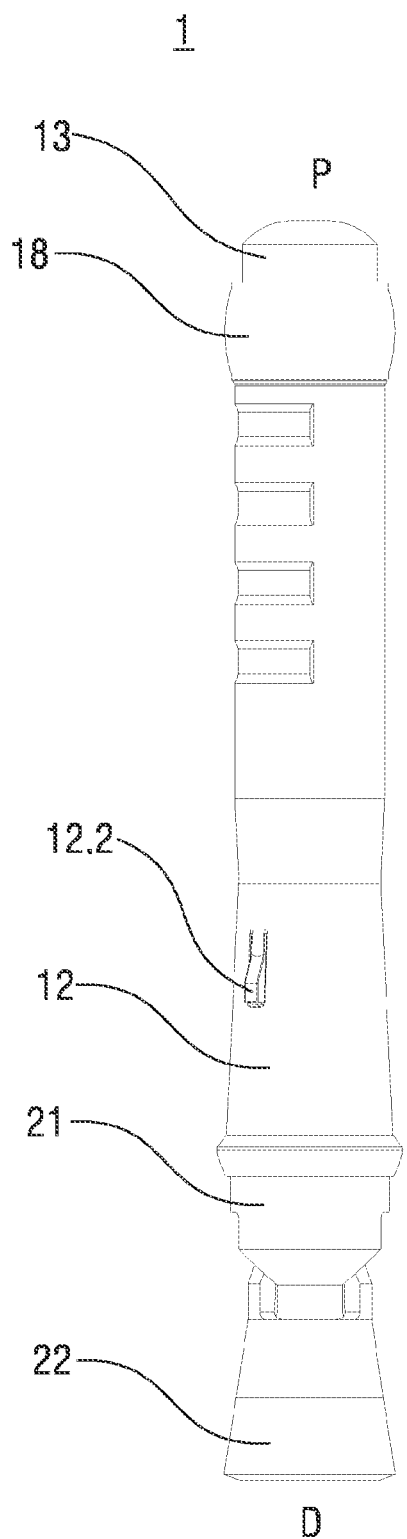
FIG. 3A shows a lateral view of an exemplary embodiment of an autoinjector according to the present invention during use.
Figure 3B:
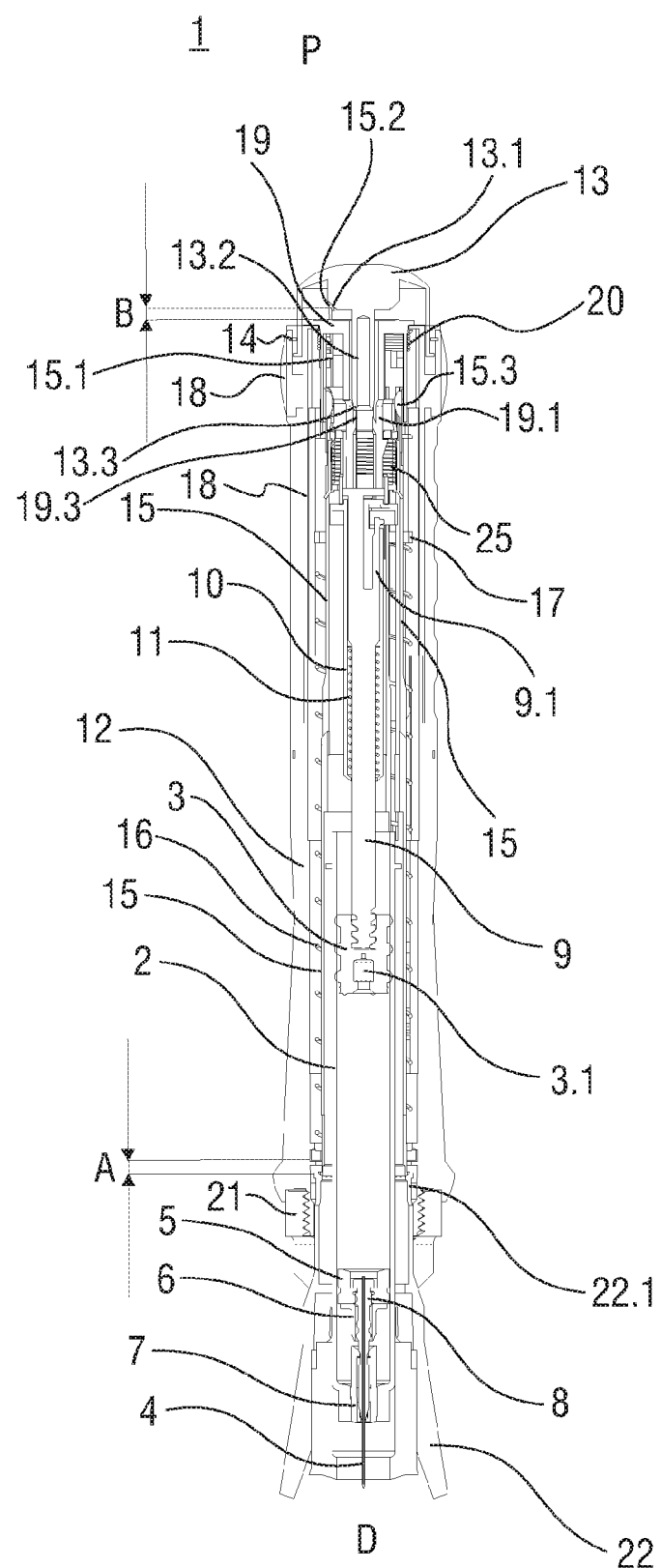
FIG. 3B shows a sectional view of an exemplary embodiment of an autoinjector according to the present invention during use.

As shown in the exemplary embodiments in FIGS. 3A and 3B, when the autoinjector 1 is pushed against an injection site, the needle sleeve 22 is pushed in the proximal direction P relative to the front case 21 and abuts and pushes the guide cylinder 15 in the proximal direction relative to the rear case 12. As a result, a distance A between a bearing grounding the distal end of the drive spring 16 in the rear case 12 and the distal end of the guide cylinder 15 is reduced. Simultaneously, the arms 15.1 on the guide cylinder 15 move in the proximal direction P increasing a distance B between the ramped latch 15.2 and the spring holder 19 so that the proximal arms 15.1 abut the ramped base 13.1 of the stem 13.2 on the trigger button 13.

Figure 4A:
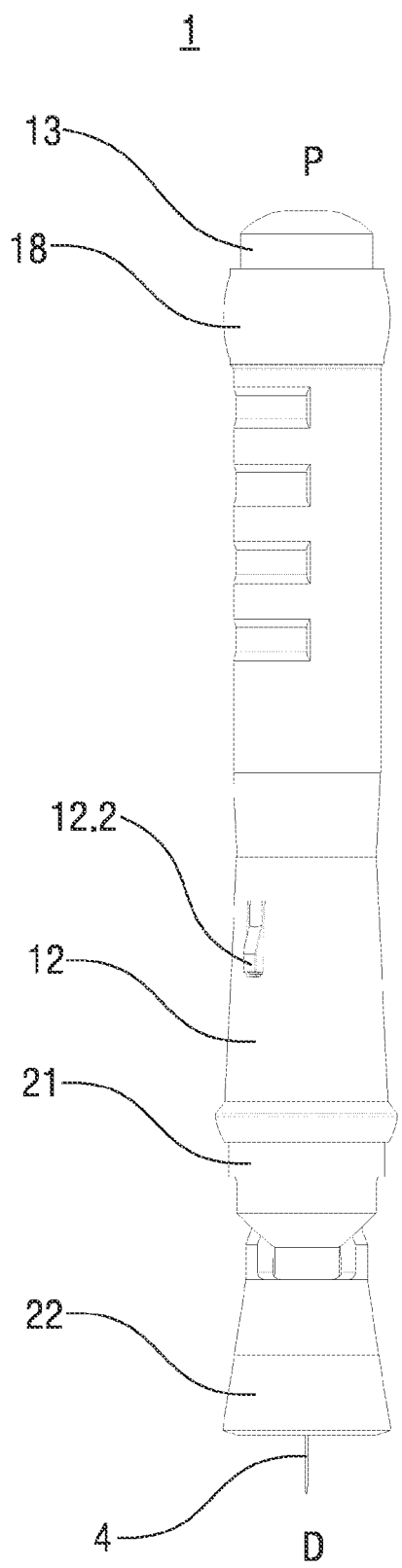
FIG. 4A shows a lateral view of an exemplary embodiment of an autoinjector according to the present invention during use.
Figure 4B:
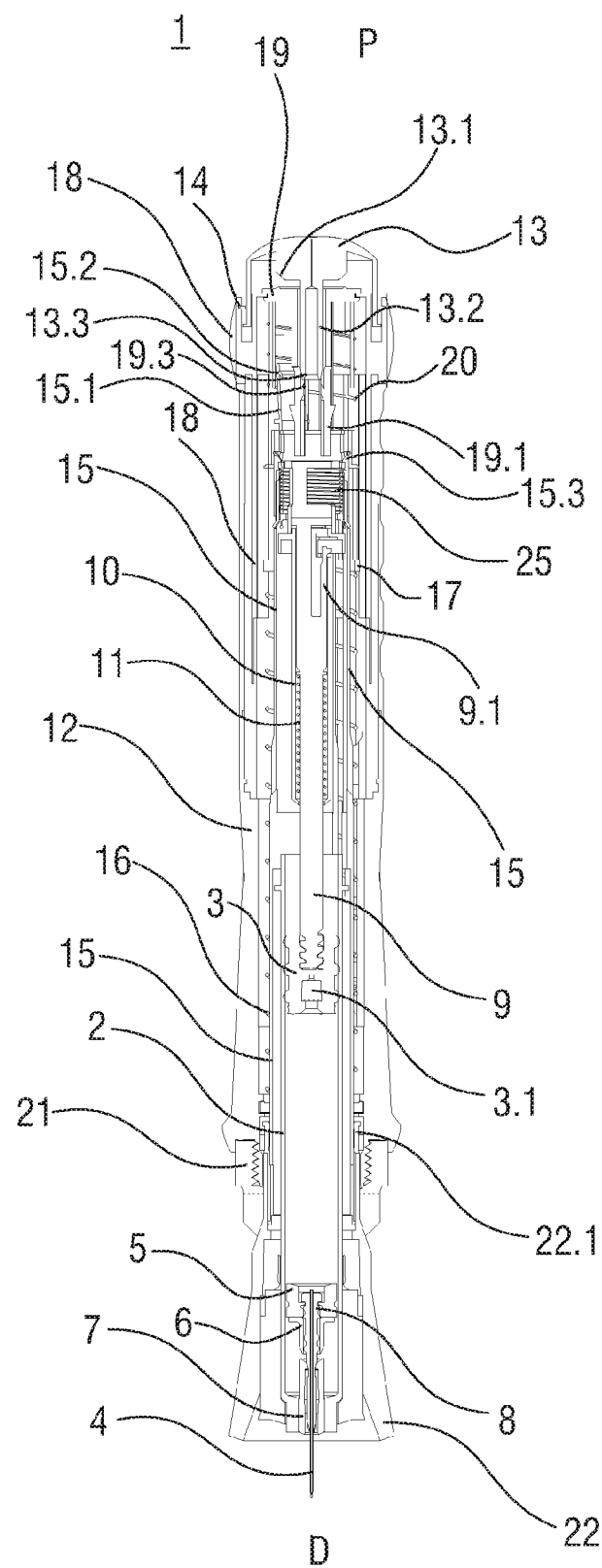
FIG. 4B shows a sectional view of an exemplary embodiment of an autoinjector according to the present invention during use.

As shown in FIGS. 4A and 4B, when the user depresses the trigger button 13, the ramped base 13.1 engages the ramped latches 15.2, deflecting them radially and disengaging the spring holder 19. Now, the guide cylinder 15 is disengaged from the spring holder 19. As the trigger button 13 is depressed further into the lead sleeve 18, the stem 13.2 engages the fingers 19.1, causing the fingers 19.1 to deflect radially. When the fingers 19.1 deflect, they disengage the spring holder 19 from the drive assembly 17. Under the force of the penetration spring 20, the guide cylinder 15 and the syringe 2 are advanced in the distal direction D relative to the rear case 12 so that the needle 4 projects from the distal end of the autoinjector 1 and penetrates the injection site. The guide cylinder 15 moves distally within the rear case 12 until it abuts a rib on the needle sleeve 22.

When the spring holder 19 disengages the drive assembly 17, the drive spring 16 pulls the drive assembly 17 in the distal direction D. As the drive assembly 17 travels distally relative to the rear case 12.1, the arms 17.1 remain deflected by an internal surface of the rear case 12.1. When the arms 17.1 reach the recesses 12.1 in the rear case 12, the arms 17.1 return to their non-deflected position and engage the recesses 12.1 to maintain an axial position of the drive assembly 17 relative to the rear case 12.

Figure 5A:
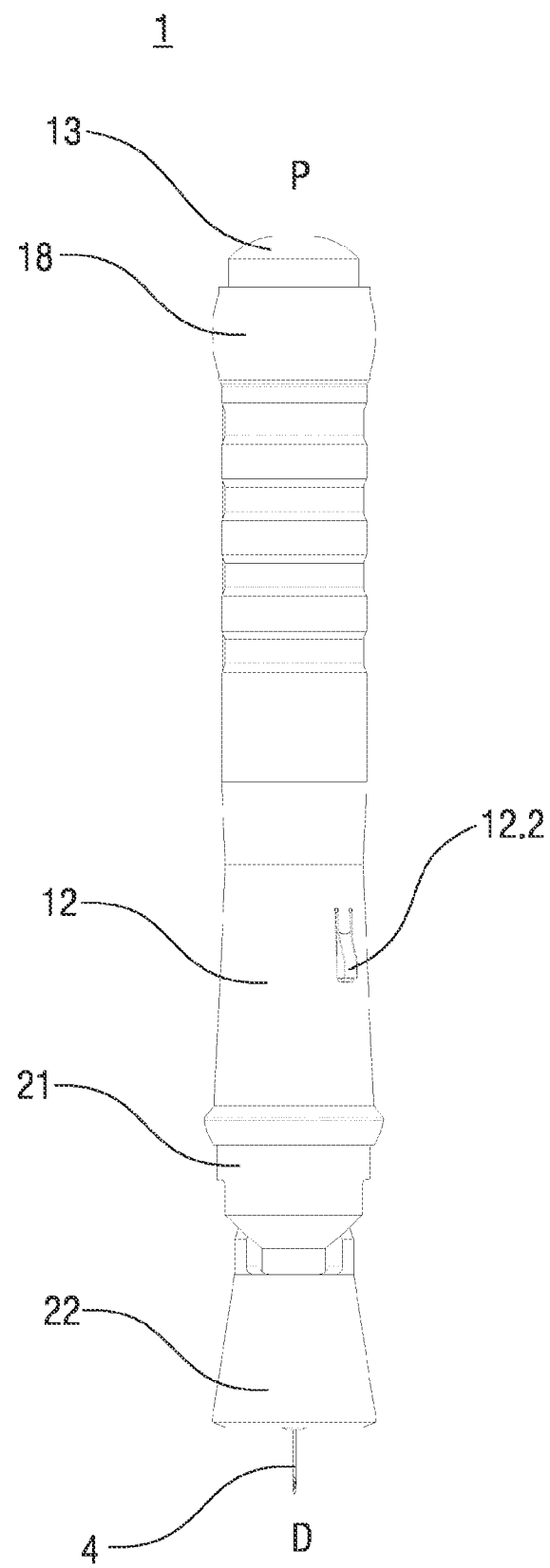
FIG. 5A shows a lateral view of an exemplary embodiment of an autoinjector according to the present invention during use.
Figure 5B:
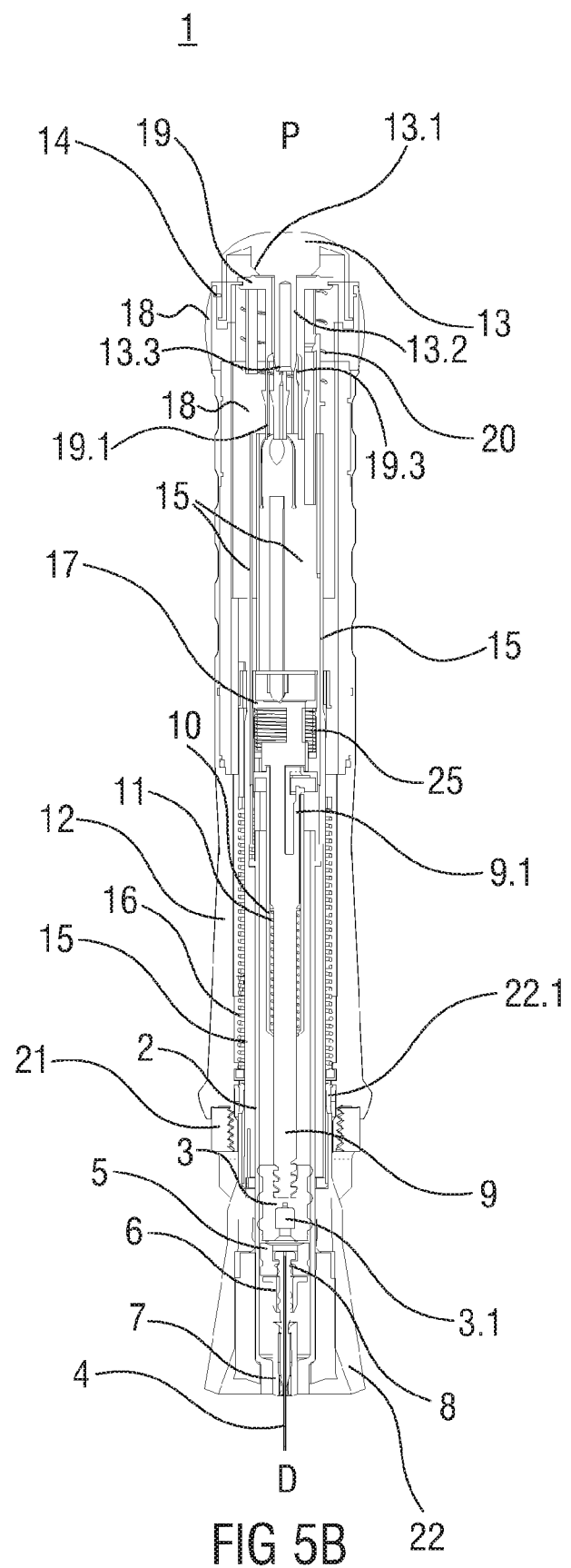
FIG. 5B shows a sectional view of an exemplary embodiment of an autoinjector according to the present invention during use.

As shown in FIGS. 5A and 5B, when the guide cylinder 15 abuts the rib on the needle sleeve 22 and is prevented from moving further distally, the drive spring 16 pulls the drive assembly 17 into engagement with the outer plunger 10. The drive assembly 17 then drives the outer plunger 10 (and the inner plunger 9 which is coupled to the outer plunger 10), displacing the stopper 3 within the syringe 2 and ejecting the medicament through the needle 4. The stopper 3 has abutted the needle seal 5.

Figure 6A:
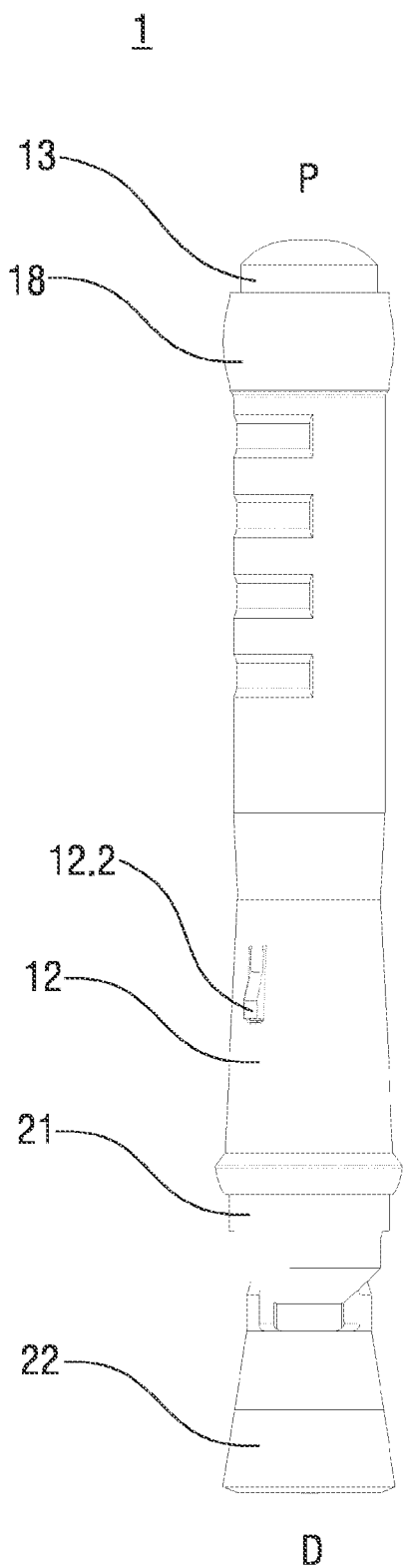
FIG. 6A shows a lateral view of an exemplary embodiment of an autoinjector according to the present invention after use.
Figure 6B:
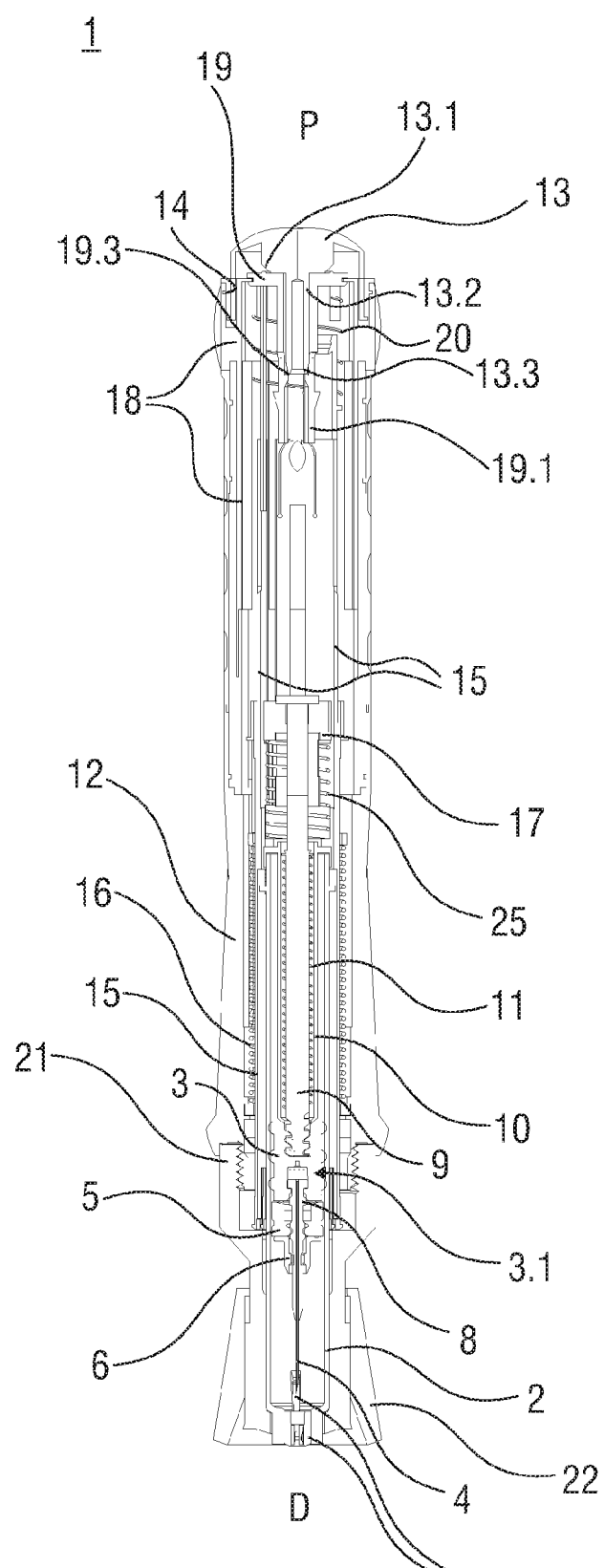
FIG. 6B shows a sectional view of an exemplary embodiment of an autoinjector according to the present invention after use.
Figure 6C:
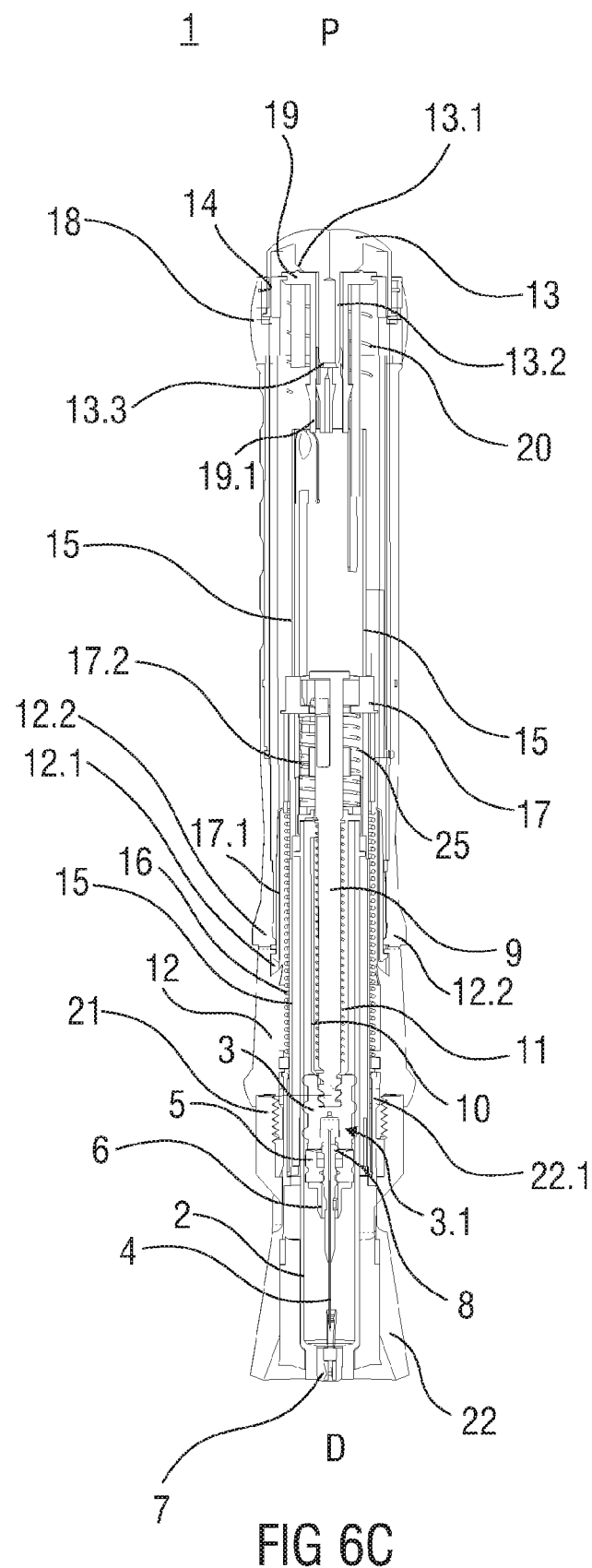
FIG. 6C shows a sectional view of an exemplary embodiment of an autoinjector according to the present invention after use.

As shown in FIGS. 6A and 6B and 6C, at or substantially near the end of a dose, the distal latches 17.2 on the drive assembly 17 are allowed to deflect, releasing the auxiliary spring 25 to push the drive assembly 17 in the distal direction D against the outer plunger 10. The auxiliary spring 25 may have a force of about 22 N.

The force provided by the auxiliary spring 25, pushes the outer plunger 10 (and inner plunger 9) to advance the stopper 3 distally within the barrel of the syringe 2. The stopper 3 pushes the ejector ring 6 into abutment with the needle retainer 7. When the ejector ring 6 engages the needle retainer 7, ramped distal arms on the ejector ring 6 deflect ramped proximal retainer arms on the needle retainer 7, releasing the needle mount 8 from the needle retainer 7. Substantially simultaneously, a proximal end of the needle mount 8 engages (e.g., frictionally, snap-fit, etc.) the cavity 3.1 in the stopper 3.

After the needle mount 9 has engaged the cavity 3.1, the release ring causes the resilient arm 9.1 on the inner plunger 9 to deflect and release the outer plunger 10. The release ring retains the outer plunger 10 in an axial position relative to the inner plunger 9. Under the force of the plunger spring 11, the inner plunger 9 (with the stopper 3 coupled to the needle mount 8) moves axially in the proximal direction P to withdraw the needle mount 8 and the needle 4 into the barrel of the syringe 2.

In an exemplary embodiment, a damping mechanism (e.g., a rubber O-ring) may be disposed in the drive assembly 17 for engaging the inner plunger 9). The damping mechanism may slow the axial movement of the inner plunger 9 to reduce pain associated with needle retraction from the injection site.

Figure 7:
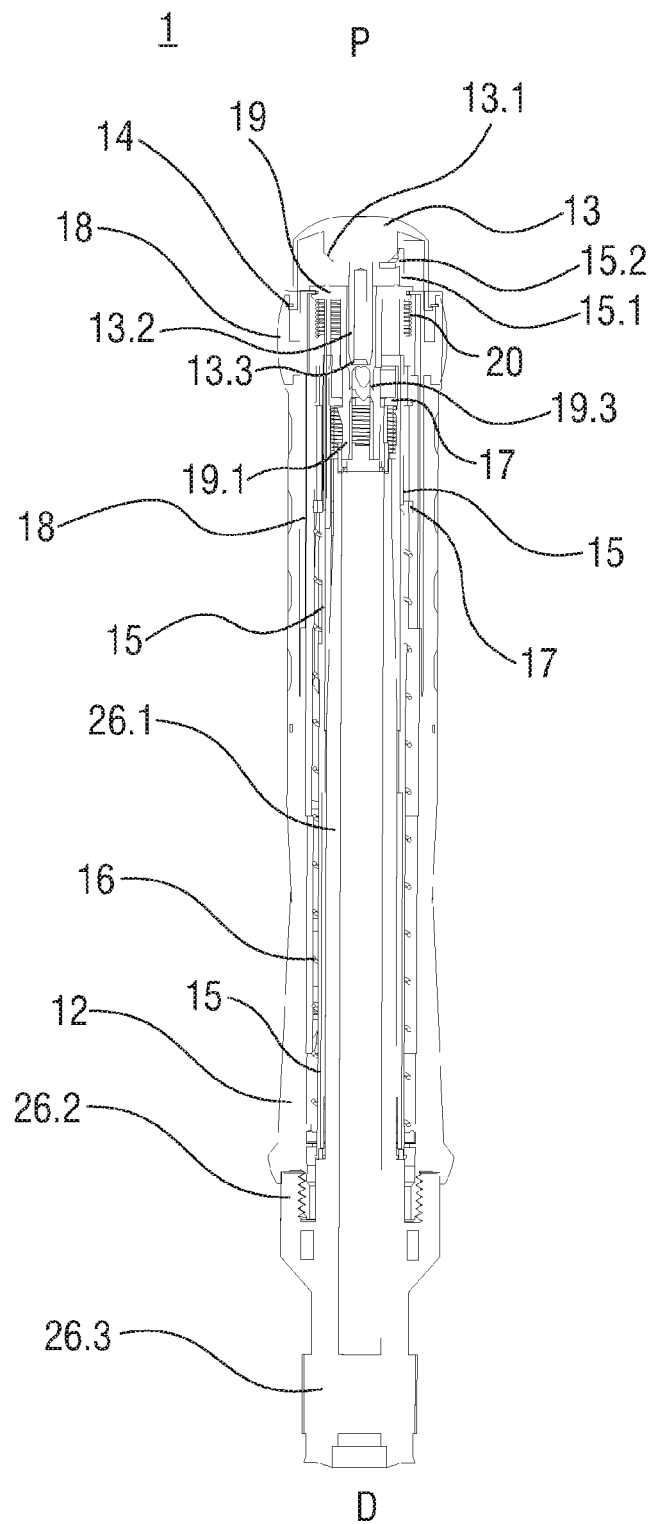
FIG. 7 shows a sectional view of an exemplary embodiment of an autoinjector and a resetting tool according to the present invention.

FIG. 7 shows an exemplary embodiment of a resetting tool 26 for resetting the autoinjector 1 for use with a new syringe 2. The rear case 12 and front case 21 may be decoupled allowing removal of the spent syringe 2. The tool 26 comprises a rod 26.1, a threaded connector 26.2 and a handle 26.3 is applied. The rod 26.1 is inserted into the guide cylinder 15 and pushed in the proximal direction P. Substantially simultaneously, the resilient arms 12.2 are pressed to deflect the arms 17.1 of the drive assembly 17 out of the recesses 12.1 on the rear case 12. Force in the proximal direction P, pushes the drive assembly 17 back into its initial position as in FIG. 1 also resetting the drive spring 16 and resetting and re-locking the auxiliary spring 25. The drive assembly 17 latches to the spring holder 19, and the ramped latches 15.2 of the guide cylinder 15 engage the spring holder 19.

The tool 26 may now be unscrewed and removed from the rear case 12. A new syringe 2 may now be inserted into the guide cylinder 15.

In another exemplary embodiment, the autoinjector 1 may be triggered simply by pushing the autoinjector 1 against the injection site. In this exemplary embodiment, the autoinjector 1 does not include the lead sleeve 18 or the trigger button 13. The spring holder 19 is engaged in the rear case 12, and a closed proximal end of the rear case 12 includes the ramped base 13.1 and the stem 13.2. The autoinjector 1 is triggered when the needle sleeve 22 is pushed against the injection site.

It goes without saying that in all ramped engagements between two components described in the above embodiments there may be just one ramp on one or the other component or there may be ramps on both components without significantly influencing the effect of the ramped engagement.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

While the exemplary embodiments are described with reference to a syringe having a needle retraction mechanism, those of skill in the art will understand that the present invention may be utilized with syringes not having any needle safety-mechanisms ro different needle-safety mechanisms. For example, if a syringe without a needle-safety mechanism is used, the autoinjector may include a syringe retraction mechanism or a protruding needle shield to ensure that the autoinjector is needle-safe before, during and after use.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. An autoinjector comprising:
a spring holder;
a guide cylinder releasably coupled to the spring holder, the guide cylinder adapted to accommodate a syringe;
a drive assembly releasably coupled to the spring holder, the drive assembly coupled to the guide cylinder;
a drive spring adapted to apply a force on the drive assembly; and
a penetration spring adapted to apply a force on the guide cylinder;
wherein the syringe includes a needle retraction mechanism including an inner plunger telescopically coupled to an outer plunger, wherein a distal end of the inner plunger is coupled to a stopper, wherein a plunger spring biases the outer plunger relative to the inner plunger, wherein a resilient arm on the inner plunger engages the inner plunger to the outer plunger, wherein a release ring on a finger flange of the syringe is adapted to engage the resilient arm, causing the arm to deflect and disengage the outer plunger, wherein when the arm disengages the outer plunger, the plunger spring expands, and the inner plunger can move axially relative to the outer plunger; and wherein the drive assembly is adapted to engage the outer plunger in use.

2. The autoinjector according to claim 1, further comprising:
a rear case adapted to engage the spring holder.

3. The autoinjector according to claim 2, wherein the drive spring is grounded in a recess in the rear case and the drive assembly.

4. The autoinjector according to claim 2, wherein the drive assembly includes resilient arms adapted to engage recesses formed in the rear case.

5. The autoinjector according to claim 2, wherein the rear case includes an enclosed end having a ramped base adapted to engage ramped latches on resilient arms on the guide cylinder and having a stem adapted to engage resilient fingers on the spring holder.

6. The autoinjector according to claim 1, further comprising:
a front case; and
a needle sleeve telescopically coupled to the front case.

7. The autoinjector according to claim 6, further comprising:
a cap detachably coupled to the front case or the needle sleeve.

8. The autoinjector according to claim 1, further comprising:
a trigger button adapted to engage the guide cylinder and the spring holder.

9. The autoinjector according to claim 8, wherein the trigger button includes a ramped base adapted to engage ramped latches on resilient arms on the guide cylinder.

10. The autoinjector according to claim 9, wherein the ramped latches releasably engage the spring holder.

11. The autoinjector according to claim 8, wherein the trigger button includes a stem adapted to engage resilient fingers on the spring holder.

12. The autoinjector according to claim 11, wherein the resilient fingers releasbly engage the drive assembly.

13. The autoinjector according to claim 1, wherein the drive spring is a tension spring.

14. The autoinjector according to claim 1, further comprising:
an auxiliary spring grounded in the drive assembly and adapted to apply a force on the outer plunger.

15. The autoinjector according to claim 14, wherein the drive assembly includes a distal resilient latch adapted to retain the auxiliary spring in a compressed state.

16. An autoinjector comprising:
a spring holder;
a guide cylinder releasably coupled to the spring holder, the guide cylinder adapted to accommodate a syringe having a plunger;
a drive assembly releasably coupled to the spring holder, the drive assembly coupled to the guide cylinder and adapted to engage the plunger;
a drive spring adapted to apply a force on the drive assembly;
a penetration spring adapted to apply a force on the guide cylinder; and
an auxiliary spring grounded in the drive assembly and adapted to apply a force on the plunger.

* * * * *